United States Patent
Wang et al.

(10) Patent No.: US 11,918,335 B2
(45) Date of Patent: Mar. 5, 2024

(54) MAGNETIC RESONANCE IMAGING METHOD, APPARATUS, AND COMPUTER STORAGE MEDIUM

(71) Applicant: SHENZHEN INSTITUTES OF ADVANCED TECHNOLOGY, Shenzhen (CN)

(72) Inventors: Haifeng Wang, Shenzhen (CN); Dong Liang, Shenzhen (CN); Hairong Zheng, Shenzhen (CN); Xin Liu, Shenzhen (CN); Shi Su, Shenzhen (CN); Zhilang Qiu, Shenzhen (CN)

(73) Assignee: SHENZHEN INSTITUTES OF ADVANCED TECHNOLOGY, Shenzhen (CN)

( * ) Notice: Subject to any disclaimer, the term of this patent is extended or adjusted under 35 U.S.C. 154(b) by 847 days.

(21) Appl. No.: 17/010,870

(22) Filed: Sep. 3, 2020

(65) Prior Publication Data

US 2020/0397335 A1    Dec. 24, 2020

Related U.S. Application Data

(63) Continuation of application No. PCT/CN2020/107359, filed on Aug. 6, 2020.

(51) Int. Cl.
*A61B 5/055* (2006.01)
*G01R 33/28* (2006.01)
*G01R 33/48* (2006.01)

(52) U.S. Cl.
CPC .............. *A61B 5/055* (2013.01); *G01R 33/28* (2013.01); *G01R 33/48* (2013.01)

(58) Field of Classification Search
CPC ......... A61B 5/055; G01R 33/28; G01R 33/48
See application file for complete search history.

(56) References Cited

U.S. PATENT DOCUMENTS

| 5,079,504 A | 1/1992 | Machida |
| 8,981,776 B2 | 3/2015 | Setsompop et al. |

(Continued)

FOREIGN PATENT DOCUMENTS

| CN | 104714199 A | 6/2010 |
| CN | 102028469 A | 4/2011 |

(Continued)

OTHER PUBLICATIONS

International Search Report, International application No. PCT/CN2020/107359, dated Nov. 5, 2021 (9 pages).

(Continued)

*Primary Examiner* — Jason M Ip

(57) ABSTRACT

A magnetic resonance imaging method includes: obtaining three-dimensional under-sampling data of a target object based on a first three-dimensional magnetic resonance imaging sequence; obtaining a three-dimensional point spread function based on the three-dimensional under-sampling data or a two-dimensional mapping data of the target object; obtaining a sensitivity map of the target object based on the data collected by three-dimensional low-resolution complete sampling; performing imaging reconstruction to the three-dimensional under-sampling data based on the three-dimensional point spread function and the sensitivity map to obtain a reconstructed magnetic resonance image. The first three-dimensional magnetic resonance imaging sequence has a first sinusoidal gradient field on a phase direction and a second sinusoidal gradient field on a layer selection direction. 0-order moments of the first and the second three-dimensional magnetic resonance imaging sequences are 0. A phase difference between the first and the second three-dimensional magnetic resonance imaging sequence is $\pi/2$.

20 Claims, 13 Drawing Sheets

(56) References Cited

U.S. PATENT DOCUMENTS

| | | |
|---|---|---|
| 2009/0134871 A1 | 5/2009 | Yui |
| 2015/0035531 A1 | 2/2015 | Stemmer |
| 2015/0192653 A1 | 7/2015 | Sharif et al. |
| 2018/0081013 A1 | 3/2018 | Taniguchi et al. |

FOREIGN PATENT DOCUMENTS

| | | |
|---|---|---|
| CN | 103961097 A | 8/2014 |
| CN | 103976735 A | 8/2014 |
| CN | 104068859 A | 10/2014 |
| CN | 104101852 A | 10/2014 |
| CN | 104459587 A | 3/2015 |
| CN | 106772167 A | 5/2017 |
| CN | 108957375 A | 12/2018 |
| CN | 109613461 A | 4/2019 |
| CN | 110133555 A | 8/2019 |

OTHER PUBLICATIONS

Zhu et al,Advances in Magnetic Resonance Tube Wall Imaging Technology and Application in Lower Extremity Atherosclerosis,Chinese Journal of Medical Imaging, Published on Dec. 31, 2014(13 pages).
Li et al,3T magnetic resonance imaging of lenticular artery based on optimized flow sensitive black blood sequence, Journal of Spectroscopy No. 04, Published on Dec. 5, 2016(22 pages).
Wu Dongmei,Study on Multiple Echo Gradient Echo Sequences with Full Flow Compensation, China Doctoral Dissertation Full Text Database Medical and Health Science and Technology Series, Published on Dec. 15, 2018(98 pages).
Hu Cuihong, Study on Data Processing Methods of Magnetic Resonance Angiography, China Excellent Master's Thesis Full Text Database Information Technology Series,Published on Mar. 15, 2011(46 pages).
Chinese first office action, Application No. 202010782357.5,dated Dec. 19, 2022(13 pages).
Bilgic et al. Wave-CAIPI for highly accelerated 3D imaging. Magnetic resonance in medicine, 2015. 73(6): p. 2152-2162.
Pruessmann et al, SENSE: sensitivity encoding for fast MRI. Magnetic resonance in medicine, 1999. 42(5): p. 952-962.
Griswold et al, Generalized autocalibrating partially parallel acquisitions (GRAPPA). Magnetic resonance in medicine, 2002. 47(6): p. 1202-1210.
Breuer et al, Controlled aliasing in volumetric parallel imaging (2D CAIPIRINHA), Magnetic resonance in medicine, 2006. 55(3): p. 549-556.
Gagoski et al, RARE/turbo spin echo imaging with simultaneous multislice Wave-CAIPI. Magnetic resonance in medicine, 2015. 73(3): p. 929-938.
Polak et al, Wave-CAIPI for highly accelerated MP-RAGE imaging. Magnetic resonance in medicine, 2018. 79(1): p. 401-406.
Wu et al, Wave-CAIPI ViSTa: highly accelerated whole-brain direct myelin water imaging with zero-padding reconstruction. Magnetic resonance in medicine, 2018.
2014 40th Annual Northeast Bioengineering Conference (NEBEC), Apr. 25, 2014 , Berkin Bilgic and so on, Wave-CAIPI Enables Highly Accelerated 3D MRI.
Basic Science Series of China Doctoral Dissertation Full Text Database, Sep. 15, 2011, Pan Wonyu, Design and Key Technology Research of a New MRI Spectrometer.
Shi Su et al: "Accelerating Three-Dimension Balanced Steady-State Free Precession Imaging with Modified Wave- CAIPI Technique", Proceedings of the International Society for Magnetic Resonance in Medicine, ISMRM,27th Annual ; Meeting and Exhibition, May 11-16, 2019, No. 4578,Apr. 26, 2019 (Apr. 26, 2019), XP040711962.
Notification to Grant Patent Right for Invention, Chinese Application No. 202010782357.5, dated Jun. 16, 2023 (6 pages).
European Search Report, European Application No. 20761130.2, dated Aug. 29, 2023 (30 pages).

MAGNETIC RESONANCE IMAGING METHOD, APPARATUS, AND COMPUTER STORAGE MEDIUM

CROSS-REFERENCE TO RELATED APPLICATIONS

The present application is a continuation-application of International (PCT) Patent Application No. PCT/CN2020/107359, filed on Aug. 6, 2020, and the entire contents of which are hereby incorporated by reference in its entirety.

TECHNICAL FIELD

The present disclosure relates to the technical field of image processing, and in particular to a magnetic resonance imaging method, a magnetic resonance imaging apparatus, and a computer non-transitory storage medium.

BACKGROUND

Magnetic resonance imaging (MRI) is non-radiative and has high resolution. Therefore, the MRI is widely applied in clinical medicine and medical researches.

A scanning speed of the MRI may be low. Scanning a patient for an excessively long period of time may cause the patient to have an unideal feeling, and at the same time, a motion artifact may be introduced while reconstructing a magnetic resonance image. In this way, quality of the reconstructed magnetic resonance image may be affected, and how to improve a speed of MRI has been a research hotspot and challenges.

Recently, a parallel imaging technique, such as a technique of generalized autocalibrating partially parallel acquisitions (GRAPPA), a technique of sensitivity encoding (SENSE), and a technique of wave controlled aliasing in parallel imaging (wave-CAIPI), is provided and dramatically reduces the scanning speed of magnetic resonance. With these fast imaging techniques, reconstruction may be performed to under-sampling data based on a sensitivity difference between receiving coils in a space, such that a part of gradient encoding may be replaced. However, a signal-to-noise rate of a reconstructed image obtained by performing the above techniques may be reduced as an acceleration time increases, and an aliasing artifact may be introduced in the reconstructed magnetic resonance image.

SUMMARY OF THE DISCLOSURE

To solve the above-mentioned problem, the present disclosure may provide a magnetic resonance imaging method. The method may include: obtaining three-dimensional under-sampling data of a target object; calculating and obtaining a three-dimensional point spread function based on the three-dimensional under-sampling data or two-dimensional mapping data of the target object, wherein the two-dimensional mapping data and the three-dimensional under-sampling data have a same field of view; calculating and obtaining a sensitivity map of the target object based on data of the target object collected by three-dimensional low-resolution complete sampling; and performing image reconstruction to the three-dimensional under-sampling data bay taking the three-dimensional point spread function and the sensitivity map to obtain a reconstructed magnetic resonance image. The three-dimensional under-sampling data is collected based on a first three-dimensional magnetic resonance imaging sequence. The first three-dimensional magnetic resonance imaging sequence may have a first sinusoidal gradient field on a phase direction and a second sinusoidal gradient field on a layer selection direction. Each of a duration of the first sinusoidal gradient field and a duration of the second sinusoidal gradient field is within a duration of a reading platform of a reading gradient field on a reading direction. A 0-order moment of the first sinusoidal gradient field and a 0-order moment of the second sinusoidal gradient field are 0. A phase difference between the first sinusoidal gradient field the second sinusoidal gradient field is $\pi/2$.

To solve the above-mentioned problem, the present disclosure may provide a magnetic resonance imaging apparatus. The apparatus may include a processor and a non-transitory memory. The processor may be coupled with the non-transitory memory. The processor is configured to execute an instruction and work with the non-transitory memory cooperatively to perform the above-mentioned magnetic resonance imaging method.

To solve the above-mentioned problem, the present disclosure may provide a computer non-transitory storage medium. The non-transitory storage medium stores a computer program, and the computer program is configured to be executed by the processor to perform the above-mentioned magnetic resonance imaging method.

BRIEF DESCRIPTION OF THE DRAWINGS

FIG. 15b shows residual images corresponding to the reconstructed coronal human brain image, the reconstructed sagittal human brain image, and the reconstructed transaxial human brain image shown in FIG. 15a.

FIG. 15c shows images of 1/g-factor of the reconstructed coronal human brain image, the reconstructed sagittal human brain image, and the reconstructed transaxial human brain image shown in FIG. 15a.

DETAILED DESCRIPTION

Figure 1:
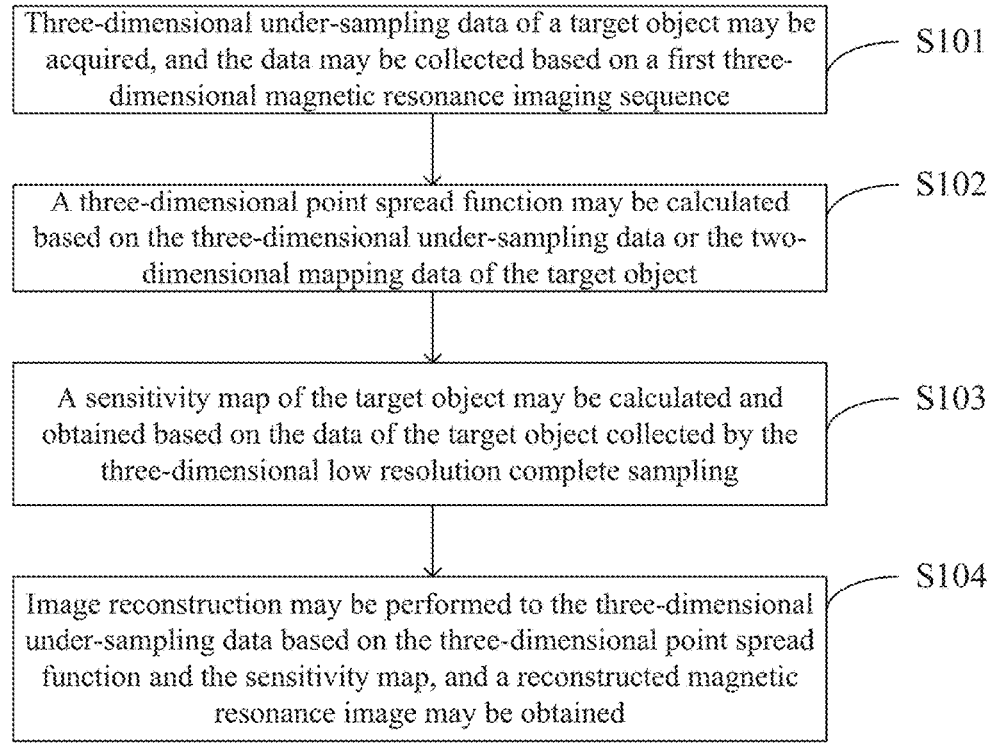
FIG. 1 is a flow chart of a magnetic resonance imaging method according to a first embodiment of the present disclosure.

To allow an ordinary skilled person in the art to understand the present disclosure better, the magnetic resonance imaging method, the magnetic resonance imaging apparatus, and the computer non-transitory storage medium provided by the present disclosure will be illustrated in details by referring to the drawings and embodiments.

A method of magnetic resonance parallel imaging, such as a technique of sensitivity encoding (SENSE), a technique of generalized autocalibrating partially parallel acquisitions (GRAPPA), and the like, is a method to increase a scanning speed of MRI. According to these techniques, an amount of data to be collected may be reduced, three-dimensional under-sampling data may be reconstructed based on redundant information included in a multi-channel coil, such that the scanning speed may be increased.

A technique of wave controlled aliasing in parallel imaging (wave-CAIPI) may be a parallel imaging technique to increase the scanning speed of three-dimensional magnetic resonance. According to the wave-CAIPI, while an MRI signal is being collected (while a reading gradient field is being applied), two sinusoidal gradient field having a phase difference of $\pi/2$ may be applied to a layer selection direction and a phase direction via an MRI gradient coil. Further, a two-dimension controlled aliasing in parallel imaging results in higher acceleration (2D CAIPIRINHA) may be performed to under-sample the data, such that an aliasing artifact caused by the under-sampling may be diffused along a reading direction, the layer selection direction, and the phase direction, an extent of the aliasing artifact for each pixel of an image may be reduced. In this way, a loss of a geometry factor (g-factor) signal-to-noise ratio of the reconstructed parallel imaging may be reduced significantly, such that a high-power acceleration may be achieved. Currently, the wave-CAIPI technique has been applied in a Turbo Spin Echo (TSE) sequence, a magnetization-prepared rapid gradient echo (MP-RAGE) sequence, a visualization of short transverse relaxation time component (ViSTa) sequence, and the like, such that a three-dimensional MRI having the high-power acceleration and high resolution has been achieved.

The wave-CAIPI technique may diffuse the aliasing artifact into the entire field of view, such that the loss of the g-factor signal-to-noise ratio may be reduced, a high-power accelerated scanning may be achieved. The 0-order moment of the applied sinusoidal gradient field on the slice selection direction or the phase direction may not be 0, an original signal of the MRI sequence may be interfered, resulting in the artifact.

To solve the above problem, the present disclosure may provide following embodiments.

As shown in FIG. 1, a flow chart of a magnetic resonance imaging method according to a first embodiment of the present disclosure is provided. The present embodiment may include following operations.

In an operation of S101, three-dimensional under-sampling data of a target object may be acquired, and the three-dimensional under-sampling data may be collected based on a first three-dimensional magnetic resonance imaging sequence.

The first three-dimensional magnetic resonance imaging sequence may refer to an imaging sequence obtained by applying wave gradient CAIPI to adjust a seventh three-dimensional magnetic resonance imaging sequence.

To be specific, based on the seventh three-dimensional magnetic resonance imaging sequence, the first three-dimensional magnetic resonance imaging sequence may include a first sinusoidal gradient field on a phase direction and a second sinusoidal gradient field on a layer selection direction. That is, a magnetic resonance system may transmit a radio frequency pulse and a gradient pulse to the target object based on the first three-dimensional magnetic resonance imaging sequence. In other words, the magnetic resonance system may transmit the radio frequency pulse and the gradient pulse of the seventh three-dimensional magnetic resonance imaging sequence to the target object, and may transmit the first sinusoidal gradient field and the second sinusoidal gradient field to the target object.

A duration of the first sinusoidal gradient field and a duration of the second sinusoidal gradient field may be within a duration of a reading platform of a reading field applied on a reading direction. The 0-order moment of the first sinusoidal gradient field and the 0-order moment of the second sinusoidal gradient field may be 0. Therefore, signals generated by the target object based on the seventh three-dimensional magnetic resonance imaging sequence within a repeated duration may not be affected, such that an additional artifact may not be introduced.

In the present embodiment, the seventh three-dimensional magnetic resonance imaging sequence may be a balanced steady-state free precession (bSSFP) sequence, a three-dimensional gradient echo (GRE) sequence, a turbo spin echo (TSE) sequence, a magnetization-prepared rapid gradient echo (MP-RAGE) sequence, a visualization of short transverse relaxation time component (ViSTa) sequence, and the like, which will not be limited by the present disclosure.

Figure 2:
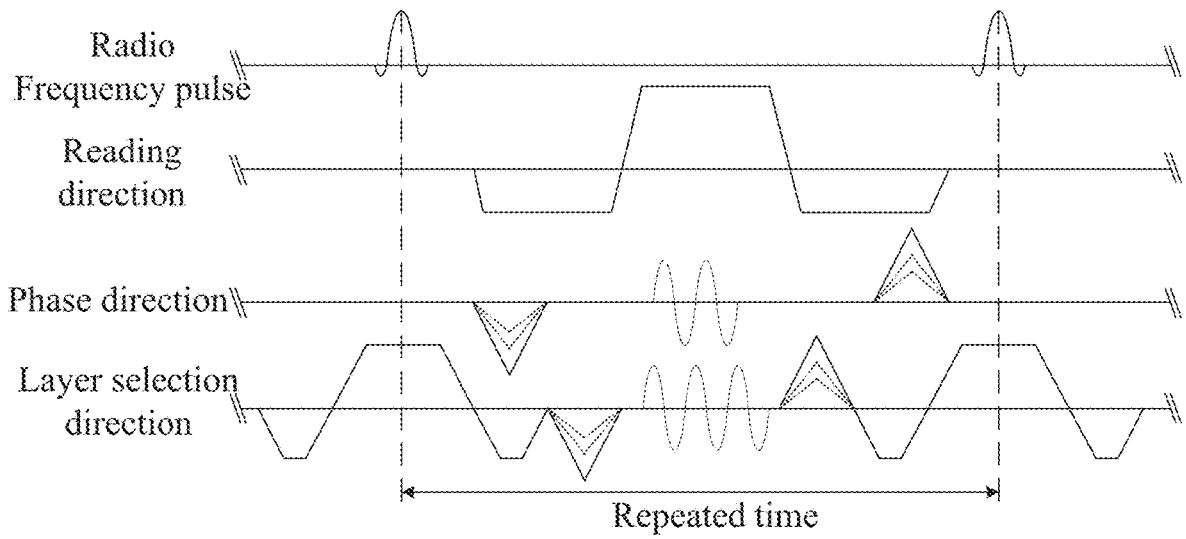
FIG. 2 is a diagram of timing of a first three-dimensional magnetic resonance imaging sequence according to an embodiment of the present disclosure.

To be exemplary, as shown in FIG. 2, FIG. 2 is a diagram of timing of a first three-dimensional magnetic resonance according to an embodiment of the present disclosure. The seventh three-dimensional magnetic resonance imaging sequence may be the bSSFP sequence.

In the present embodiment, the 0-order moment of the first sinusoidal gradient field and the 0-order moment of the second sinusoidal gradient field being 0 may refer to, in the first three-dimensional magnetic resonance imaging sequence and within various closed regions defined by the first sinusoidal gradient field and a time axis, an area of a closed region defined above the time axis being equal to an area of a closed region defined below the time axis; and in the first three-dimensional magnetic resonance imaging sequence and within various closed regions defined by the second sinusoidal gradient field and a time axis, an area of a closed region defined above the time axis being equal to an area of a closed region defined below the time axis.

A first duration of applying the first sinusoidal gradient field on the phase direction may be an integer number of times of a sinusoidal period, such as 1 time, 2 times, 5 times, 10 times, and the like. A second duration of applying the second sinusoidal gradient field on the layer selection direction may be an integer number of times of a sinusoidal period, such as 1 time, 2 times, 5 times, 10 times, 20 times, and the like. The first duration and the second duration may be less than or equal to the duration of the reading platform $D_R$ of the reading gradient field. The first duration may be less than the second duration, and the first duration and the second duration may be adjusted based on the duration of the reading platform of the reading gradient field and the sinusoidal period, which will not be limited by the present disclosure.

Further, a sinusoidal frequency of the first sinusoidal gradient field may be equal to a sinusoidal frequency of the second sinusoidal gradient field, and a phase difference between the first sinusoidal gradient field and the second sinusoidal gradient field may be π/2.

First time when the first sinusoidal gradient field being applied may be earlier than an odd number time of a quarter sinusoidal period of second time when the second sinusoidal gradient field being applied, the odd number time may be 1 time, 3 times, 5 times, 7 times, and the like. That is, the first time may be earlier than a quarter sinusoidal period of the second time, three quarters of the sinusoidal period of the second time, five quarters of the sinusoidal period of the second time, seven quarters of the sinusoidal period of the second time, or the like. Of course, the first time may be later than the odd number time of the quarter sinusoidal period of the second time.

Figure 3:
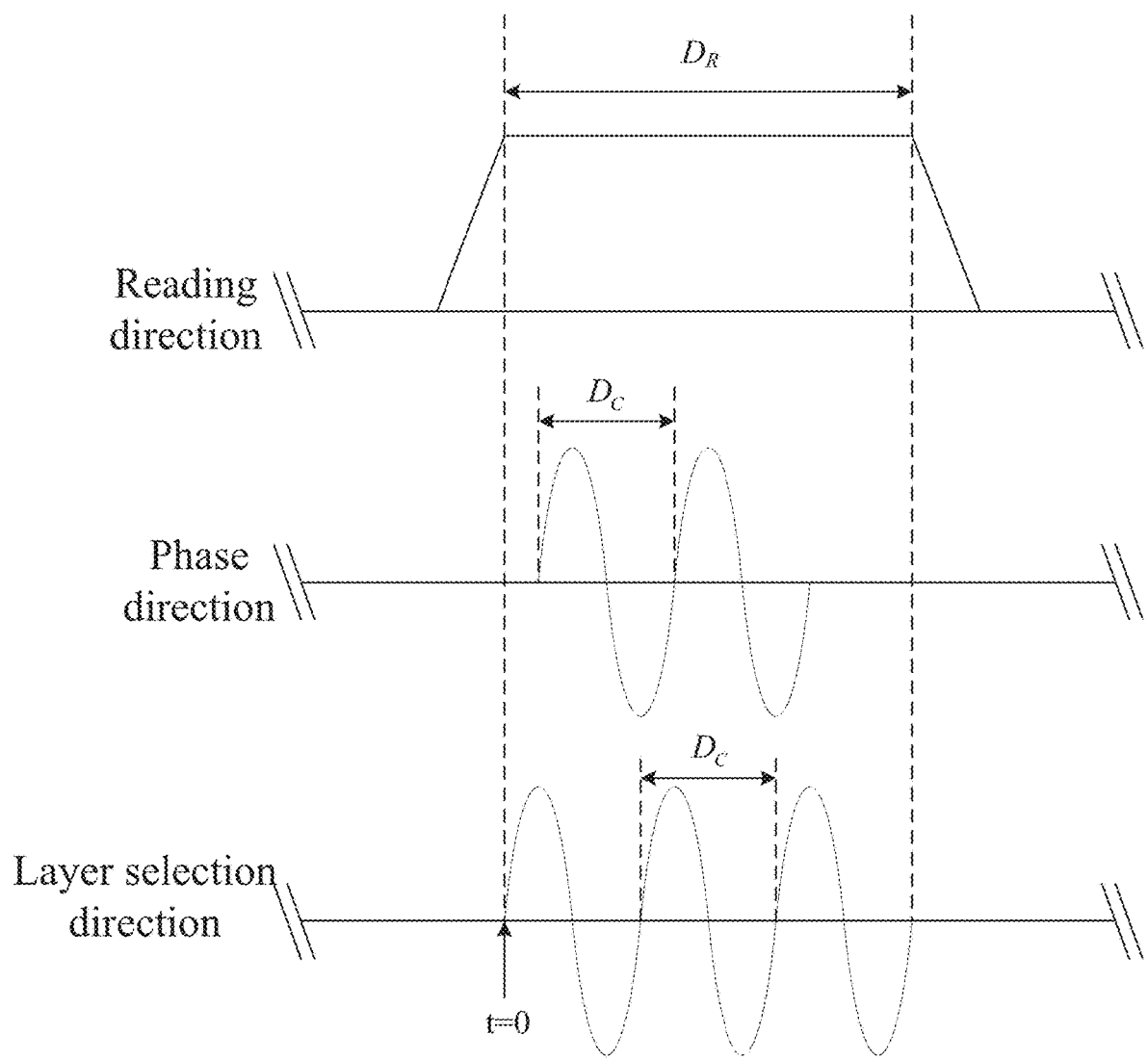
FIG. 3 is a diagram of timing of a first sinusoidal gradient field and a second sinusoidal gradient field according to an embodiment of the present disclosure.
Figure 4:
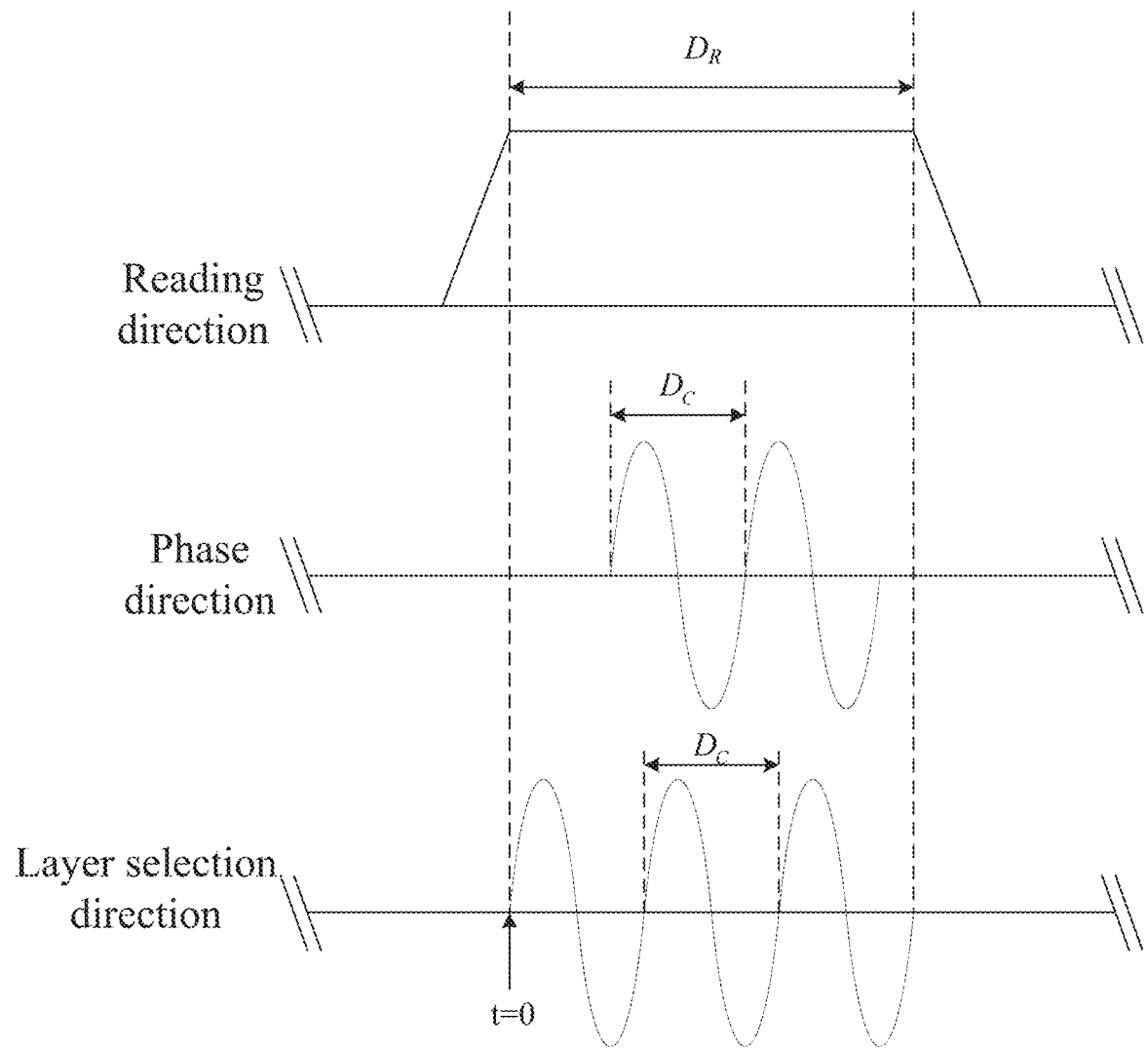
FIG. 4 is a diagram of timing of a first sinusoidal gradient field and a second sinusoidal gradient field according to another embodiment of the present disclosure.
Figure 5:
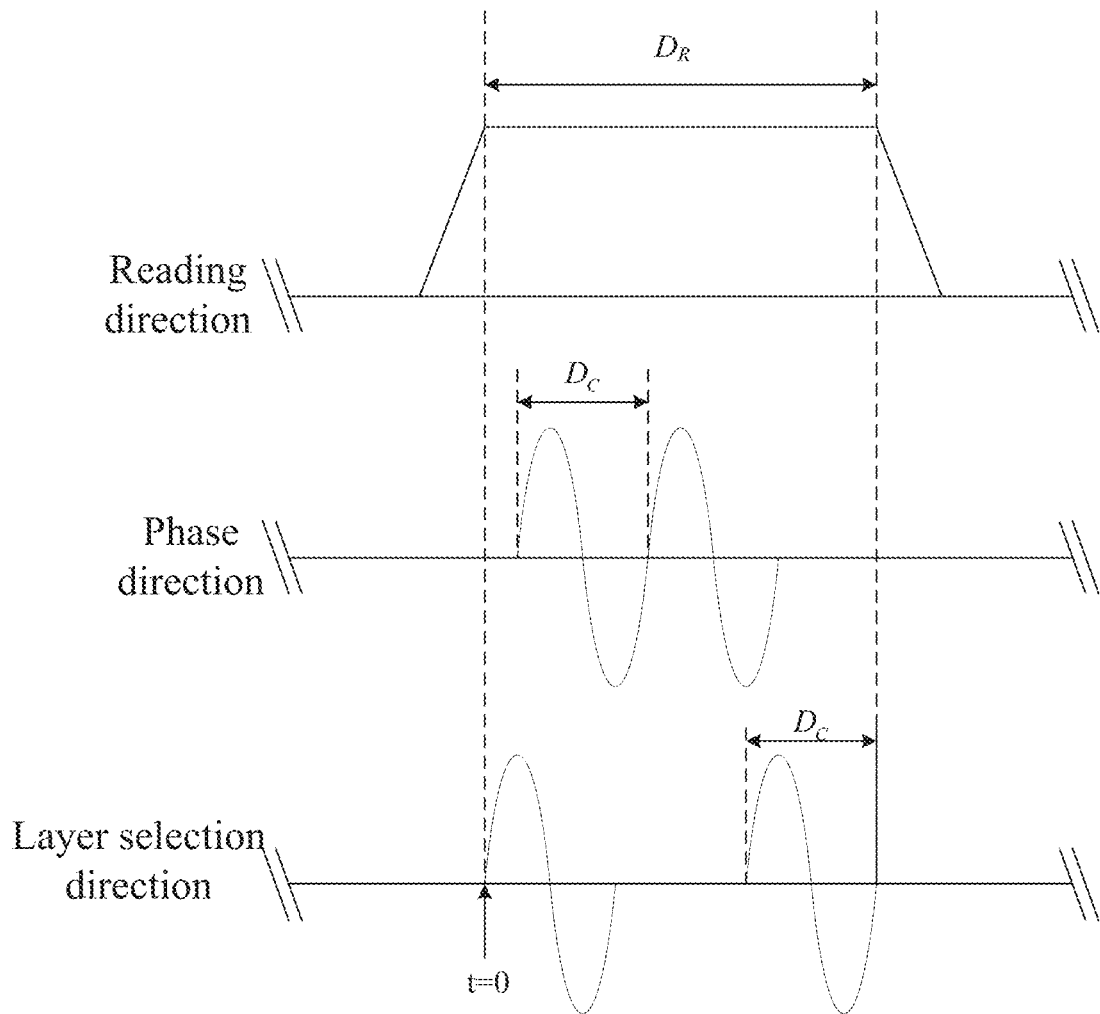
FIG. 5 is a diagram of timing of a first sinusoidal gradient field and a second sinusoidal gradient field according to still another embodiment of the present disclosure.
Figure 6:
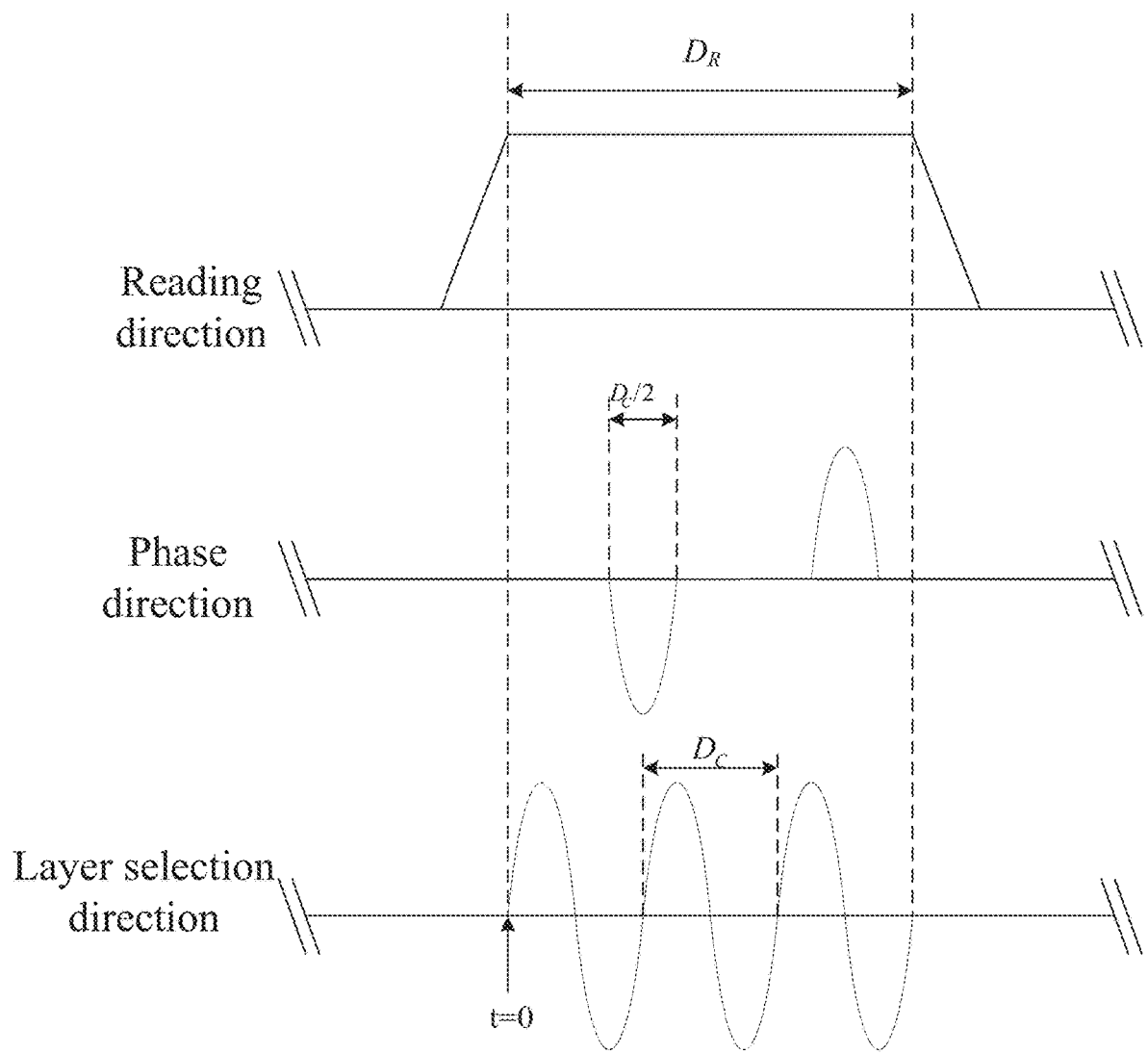
FIG. 6 is a diagram of timing of a first sinusoidal gradient field and a second sinusoidal gradient field according to still another embodiment of the present disclosure.
Figure 7:
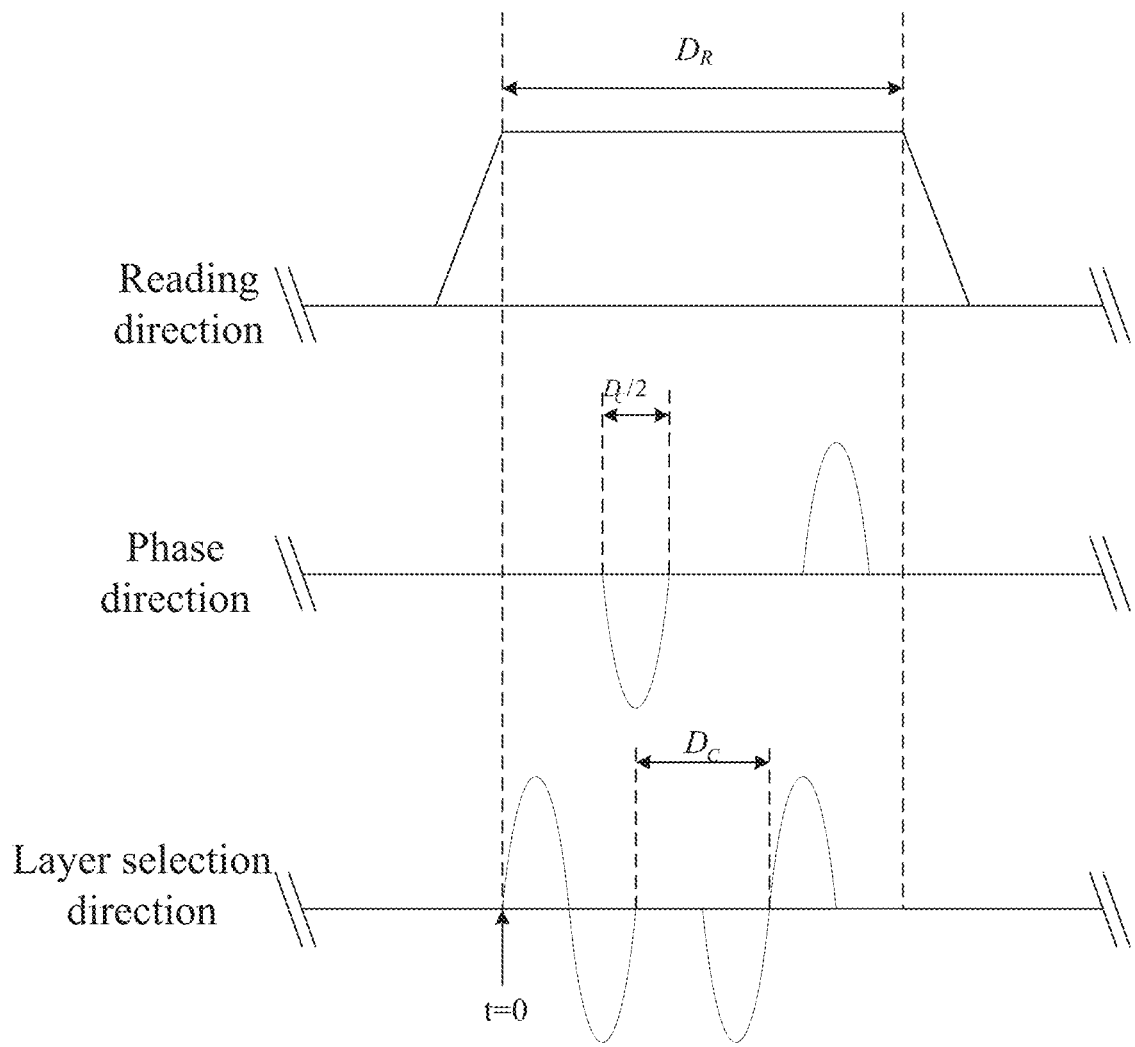
FIG. 7 is a diagram of timing of a first sinusoidal gradient field and a second sinusoidal gradient field according to still another embodiment of the present disclosure.
Figure 8:
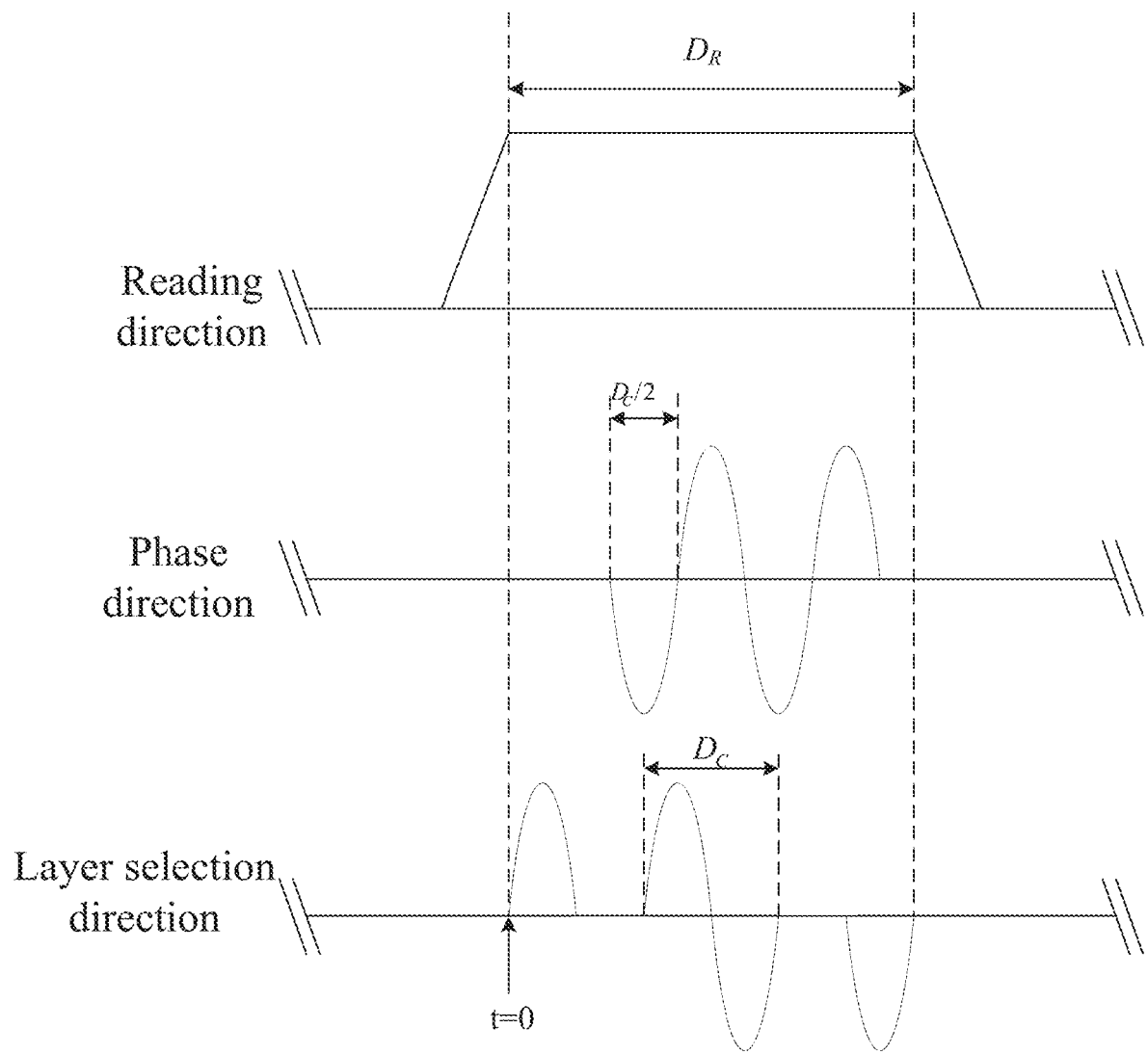
FIG. 8 is a diagram of timing of a first sinusoidal gradient field and a second sinusoidal gradient field according to still another embodiment of the present disclosure.

The first sinusoidal gradient field and the second sinusoidal gradient field may be in various forms, as shown in FIGS. 3 to 8. FIG. 3 is a diagram of timing of a first sinusoidal gradient field and a second sinusoidal gradient field according to an embodiment of the present disclosure. FIG. 4 is a diagram of timing of a first sinusoidal gradient field and a second sinusoidal gradient field according to another embodiment of the present disclosure. FIG. 5 is a diagram of timing of a first sinusoidal gradient field and a second sinusoidal gradient field according to still another embodiment of the present disclosure. FIG. 6 is a diagram of timing of a first sinusoidal gradient field and a second sinusoidal gradient field according to still another embodiment of the present disclosure. FIG. 7 is a diagram of timing of a first sinusoidal gradient field and a second sinusoidal gradient field according to still another embodiment of the present disclosure. FIG. 8 is a diagram of timing of a first sinusoidal gradient field and a second sinusoidal gradient field according to still another embodiment of the present disclosure. In the FIGS. 3 to 8, the first time, the second time, the number of the sinusoidal periods of the first sinusoidal gradient field, and the number of the sinusoidal periods of the second sinusoidal gradient field may be exemplary only, and may not be limited by the present disclosure.

It may be understood that, in the present embodiment, the first sinusoidal gradient field and the second sinusoidal gradient field may be obtained by performing a phase shift, a phase truncation, and a combination thereof on a sinusoidal gradient field or a cosinusoidal gradient field, such as the first sinusoidal gradient field shown in the FIGS. 3 to 8. For example, as shown in FIG. 5, the first sinusoidal gradient field may be obtained by truncating a half period (−π/4 to π/4) of a cosinusoidal wave, and that is, an initial direction of the first sinusoidal gradient being applied and an initial direction of the second sinusoidal gradient field being applied may be reversed.

The first sinusoidal gradient field and the second sinusoidal gradient field may be expressed by a formula. An embodiment shown in FIG. 3 may be taken as an example.

A formula representing the first sinusoidal gradient field may be shown as follows:

$$G_y(t) = \begin{cases} A\sin\left(2\pi \cdot \dfrac{t}{D_C} + \dfrac{\pi}{2}\right) & D_C \cdot \dfrac{a}{4} \le t \le D_C \cdot \dfrac{a}{4} + bD_C \\ 0 & 0 \le t < D_C \cdot \dfrac{a}{4} \text{ or } D_C \cdot \dfrac{a}{4} + bD_C < t \le D_R \end{cases}$$

A formula representing the second sinusoidal gradient field may be shown as follows:

$$G_z(t) = \begin{cases} A\sin\left(2\pi \cdot \dfrac{t}{D_C}\right) & D_C \cdot \dfrac{c}{2} \le t \le D_C \cdot \dfrac{c}{2} + dD_C \\ 0 & 0 \le t < D_C \cdot \dfrac{c}{2} \text{ or } D_C \cdot \dfrac{c}{2} + dD_C < t \le D_R \end{cases}$$

In the above formula, the t may indicate time, the A may indicate an amplitude of the sinusoidal gradient field, the Dc may indicate a duration of the sinusoidal gradient field, and the $D_R$ may indicate the duration of the reading platform of the reading gradient field. The a may be a positive odd number, the b may be a positive natural number, the c may be a positive natural number, and the d may be a positive natural number. The bDc may indicate the first duration, the dDc may indicate the second duration, the bDc and the cDc may both be less than the $D_R$. t=0 may indicate a start time of the reading platform, and indicate an original point herein.

With the first sinusoidal gradient field and the second sinusoidal gradient field, a readout spatial trace K may be in a spiral form along the reading direction. In this way, it may be understood that, the three-dimensional point spread function may be applied to enable each voxel of the target object to be diffused along the reading direction. Therefore, in an aliasing portion of the image collected by parallel imaging, a coil sensitivity difference between aliasing voxels may be increased, such that, while performing reconstruction, the g-factor may infinitely approach to 1, and amplification of the noise may be reduced. Within the duration of the reading platform of the reading gradient field, the first sinusoidal gradient field may be applied, and the 0-order moment of the first sinusoidal gradient field and the 0-order moment of the second sinusoidal gradient field may be 0. In this way, within a repeated period of time, the first sinusoidal gradient field and the second sinusoidal gradient field may not interfere the magnetic resonance signals generated by the target object based on the first magnetic resonance imaging sequence, such that the additional artifact may not be introduced while reconstructing the magnetic resonance image.

Further, based on conventional multi-layer simultaneous excitation, under-sampling data may be applied with the wave gradient CAIPI, and the magnetic resonance signal generated by the target object based on the first three-dimensional magnetic resonance imaging sequence may be under-sampled, and three-dimensional under-sampling data may be obtained. The under-sampling data may allow a coverage area of the space K to remain unchanged, but allow a distance between adjacent phase encoding lines and a distance between adjacent slice selection encoding lines to be increased. In the space K, increasing the distance between adjacent phase encoding lines and the distance between adjacent slice selection encoding lines may suggest that the field of view in an image domain is reduced. That is, an inverse-Fourier transformation may be performed to transfer the space K after the sampling into the image domain, and an aliasing of images may be caused. The aliasing artifact may be eliminated by a subsequent reconstruction algorithm, such as reconstructing the three-dimensional under-sampling data based on a sensitivity map, which will be described in details hereinafter.

The under-sampling data may be the 2D CAIPIRINHA, the SENSE in parallel imaging, GRAPPA, or the like, which will not be limited by the present disclosure.

In the present embodiment, the 2D CAIPIRINHA is taken as an example to illustrate performing under-sampling to the magnetic resonance signal. Different from performing data sampling in a conventional parallel imaging method, the 2D CAIPIRINHA may enable the aliasing artifact caused by under-sampling to be diffused to the phase direction and the layer selection direction. A background region of the view may be utilized more effectively, the sensitivity difference between aliasing pixels may be increased, such that the g-factor may be reduced, and the artifact resulted during reconstruction may be reduced.

Figure 9:
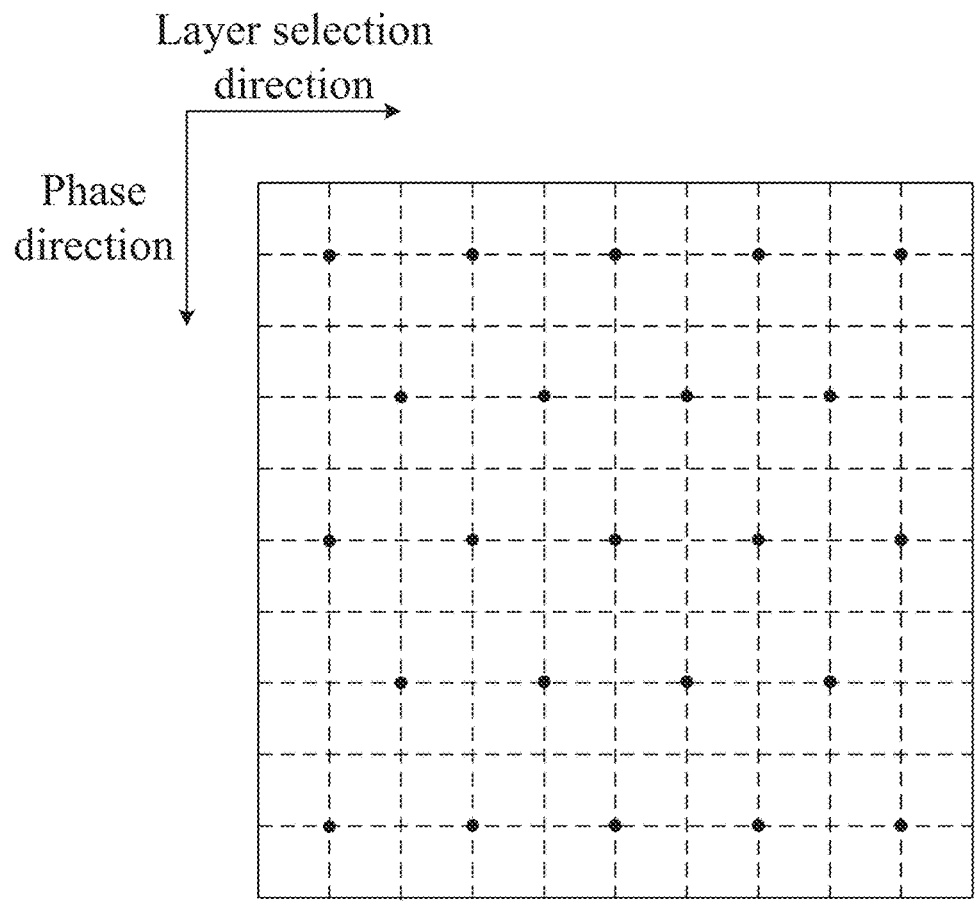
FIG. 9 is a diagram of performing wave controlled aliasing in parallel imaging (wave CAIPI) to under-sample a magnetic resonance signal.

To be exemplary, as shown in FIG. 9, FIG. 9 is a diagram of performing the 2D CAIPIRINHA to under-sample a magnetic resonance signal. In FIG. 9, a direction perpendicular to the present plane (also perpendicular to the phase direction and the layer selection direction) may be the reading direction. An intersection between black dotted lines may be a reading line to be collected by complete sampling. In the present embodiment, a reading line to be collected by under-sampling may be indicated by a bold filled dot. FIG. 7 shows a 2×2 times of under-sampling (2 times of under-sampling along the phase direction, 2 times of under-sampling along the layer selection direction), a total number of times of acceleration may be 4, time consumed for sampling=repeated time (TR)×the number of phase encoding lines (Np)×the number of layer selection lines (Ns)/4.

In an operation of S102, the three-dimensional point spread function may be calculated based on the three-dimensional under-sampling data or the two-dimensional mapping data of the target object.

The three-dimensional point spread function may be configured to calibrate a sampling trace of the space K.

The three-dimensional point spread function may be calculated by various means, such as calculated based on the three-dimensional under-sampling data. To be specific, the three-dimensional under-sampling data may be calculated by a joint estimation method, and an operation of iterative optimization may be performed to obtain the three-dimensional point spread function.

The three-dimensional point spread function may also be obtained by collecting and calculating the two-dimensional mapping data.

The two-dimensional mapping data may include a first two-dimensional mapping data, a second two-dimensional mapping data, a third two-dimensional mapping data, and a fourth two-dimensional mapping data. Each of the first two-dimensional mapping data, the second two-dimensional mapping data, the third two-dimensional mapping data, the fourth two-dimensional mapping data, and the three-dimensional under-sampling data may have a same view.

Figure 10:
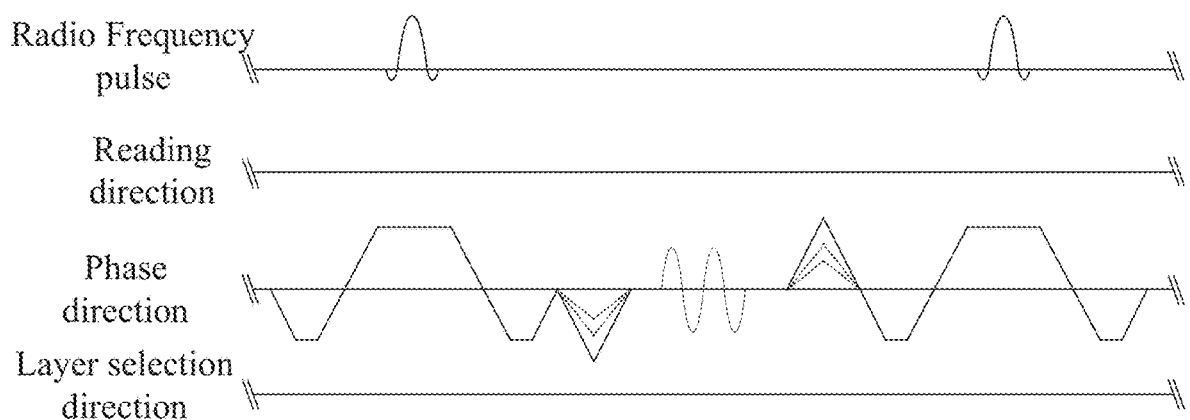
FIG. 10 is a diagram of timing of a second three-dimensional magnetic resonance imaging sequence according to an embodiment of the present disclosure.
Figure 11:
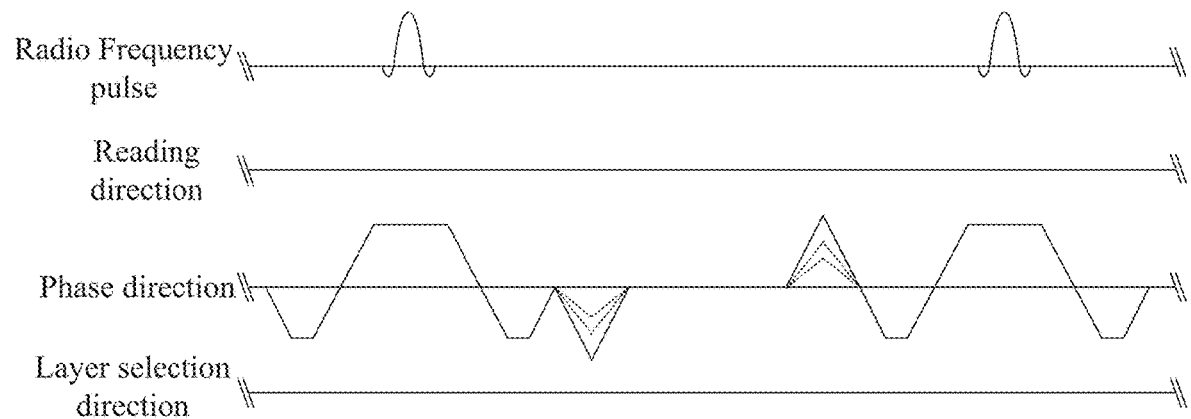
FIG. 11 is a diagram of timing of a third three-dimensional magnetic resonance imaging sequence according to an embodiment of the present disclosure.
Figure 12:
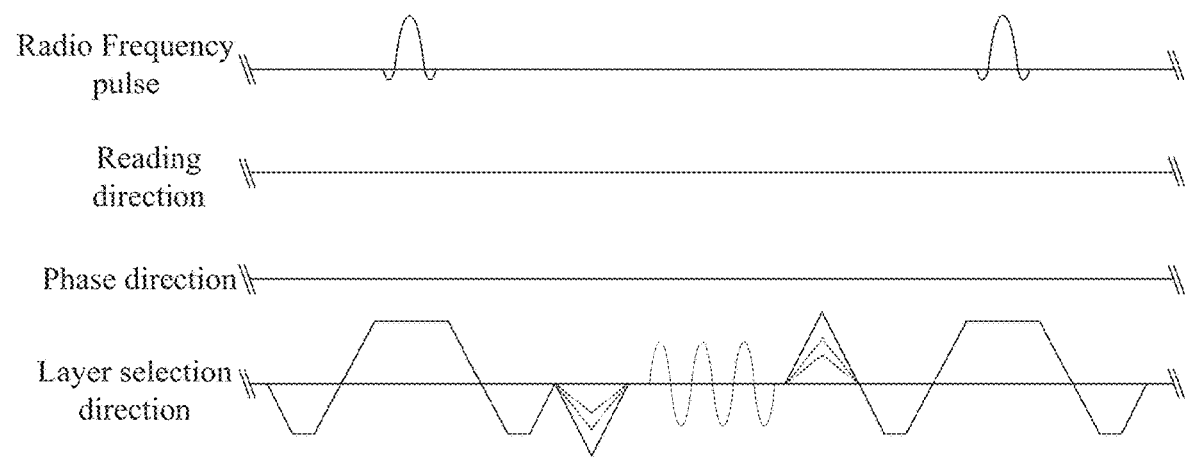
FIG. 12 is a diagram of timing of a fourth three-dimensional magnetic resonance imaging sequence according to an embodiment of the present disclosure.
Figure 13:
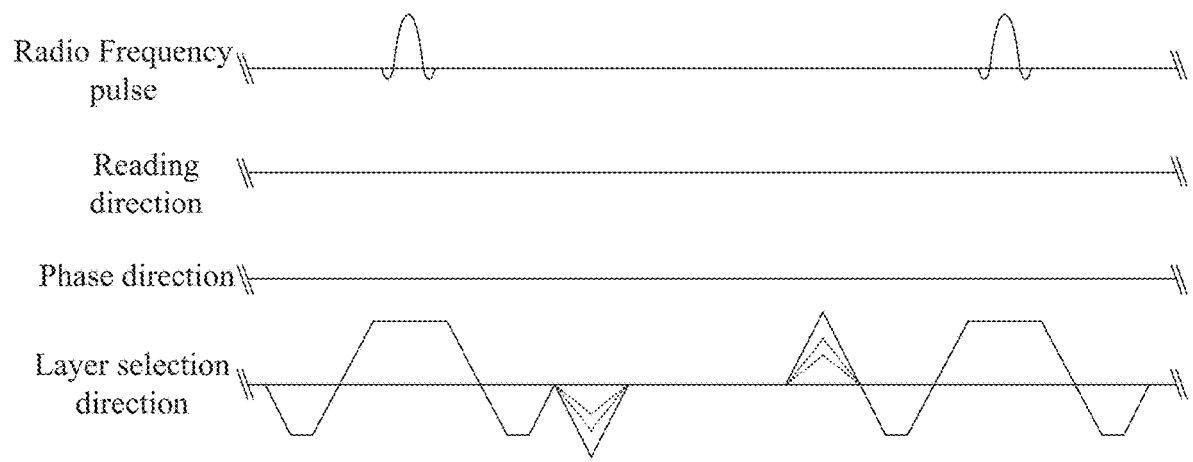
FIG. 13 is a diagram of timing of a fifth three-dimensional magnetic resonance imaging sequence according to an embodiment of the present disclosure.

As shown in FIGS. 10 to 13, FIG. 10 is a diagram of timing of a second three-dimensional magnetic resonance imaging sequence according to an embodiment of the present disclosure. FIG. 11 is a diagram of timing of a third three-dimensional magnetic resonance imaging sequence according to an embodiment of the present disclosure. FIG. 12 is a diagram of timing of a fourth three-dimensional magnetic resonance imaging sequence according to an embodiment of the present disclosure. FIG. 13 is a diagram of timing of a fifth three-dimensional magnetic resonance imaging sequence according to an embodiment of the present disclosure. Sequences shown in the FIGS. 10 to 13 may only be exemplary, and may not be limited by the present disclosure.

The first two-dimensional mapping data may be collected based on a pulse corresponding to the second three-dimensional magnetic resonance imaging sequence applying to the target object. The second two-dimensional mapping data may be collected based on a pulse corresponding to the third three-dimensional magnetic resonance imaging sequence applying to the target object. The third two-dimensional mapping data may be collected based on a pulse corresponding to the fourth three-dimensional magnetic resonance imaging sequence applying to the target object. The fourth two-dimensional mapping data may be collected based on a pulse corresponding to the fifth three-dimensional magnetic resonance imaging sequence applying to the target object.

A phase direction of the second three-dimensional magnetic resonance imaging sequence may include a first sinusoidal gradient field and a first gradient field, as shown in FIG. 10. A phase direction of the third three-dimensional magnetic resonance imaging sequence may include the first gradient field but preclude the first sinusoidal gradient field, as shown in FIG. 11. A layer selection direction of the fourth three-dimensional magnetic resonance imaging sequence may include a second sinusoidal gradient field and the first gradient field, as shown in FIG. 12. A layer selection direction of the fifth three-dimensional magnetic resonance imaging sequence may include the first gradient field but preclude the second sinusoidal gradient field, as shown in FIG. 13. Further, a gradient field of the layer selection direction of the first gradient field may be the same as a gradient field of the layer selection direction of the seventh gradient field. In this way, an accuracy of calibrating a trace of complete-sampling data of three-dimensional low resolution based on the two-dimensional mapping data may be increased. Of course, the timing diagrams of the first gradient fields shown in FIGS. 10 and 12 may be exemplary only, and the first gradient field may be another gradient field.

In summary, time consumed for collecting first two-dimensional mapping data and second two-dimensional mapping data may be 2×repeated time (TR)×the number of phase encoding lines (Np). Time consumed for collecting third two-dimensional mapping data and fourth two-dimensional mapping data may be 2×repeated time (TR)×the number of layer selection encoding lines (Ns). As the above-mentioned mapping data may be collected two-dimensional data, time consumed for scanning may be relatively short, and an efficiency of scanning the target object may be increased.

Based on the first two-dimensional mapping data and the second two-dimensional mapping data along the phase direction, a two-dimensional point spread function along the phase direction may be obtained. To be specific, the first two-dimensional mapping data may be divided by the second two-dimensional mapping data to obtain the two-dimensional point spread function of the phase direction. A formula of the calculation may be shown as follows:

$$PSF_y(k_x,y) = waveP_y(k_x,y)/P_y(k_x,y)$$

In the above formula, the $waveP_y(k_x, y)$ may be the first two-dimensional mapping data of any point $(k_x, y)$ along the phase direction. The $P_y(k_x, y)$ may be the second two-dimensional mapping data of any point $(k_c, y)$ along the phase direction. The $PSF_y(k_x, y)$ may be a value of the point spread function of any point $(k_x, y)$ in the two-dimensional point spread function $PSF_y$.

Based on the third two-dimensional mapping data and the fourth two-dimensional mapping data along the layer selection direction, a two-dimensional point spread function along the layer selection direction may be obtained. To be specific, the third two-dimensional mapping data may be divided by the fourth two-dimensional mapping data to obtain the two-dimensional point spread function of the layer selection direction. A formula of the calculation may be shown as follows:

$$PSF_z(k_x,z) = waveP_z(k_x,z)/P_z(k_x,z)$$

In the above formula, the $waveP_z(k_x, z)$ may be the third two-dimensional mapping data of any point $(k_x, z)$ along the layer selection direction. The $P_z(k_x, z)$ may be the fourth two-dimensional mapping data of any point $(k_x, z)$ along the layer selection direction. The $PSF_z(k_x, z)$ may be a point spread value of any point $(k_x, z)$ of the two-dimensional point spread function along the layer selection direction.

After the phase two-dimensional point spread function and the layer selection two-dimensional point spread function are determined, the three-dimensional point spread function may be obtained based on the two two-dimensional point spread functions. A formula for calculating the three-dimensional point spread function may be shown as follows:

$$PSF_{yz}(k_x,y,z) = PSF_z(k_x,z) \cdot PSF_y(kx,y)$$

In the above formula, the $PSF_{yz}(k_x, y, z)$ may a three-dimensional point spread value of any three-dimensional point $(k_z, y, z)$ in the three-dimensional point spread function $PSF_{yz}$.

Compared to determining the three-dimensional point spread function based on the three-dimensional mapping data, collecting the two-dimensional mapping data along the phase direction and the layer selection direction may reduce the time consumed for collecting the mapping data, such that the time consumed for collecting the MRI data may be reduced.

In an operation of S103, a sensitivity map of the target object may be calculated and obtained based on the data of the target object collected by the three-dimensional low resolution complete sampling.

In order to increase the speed of collecting the magnetic resonance image data, the CAIPIRINHA may be performed in the present embodiment to under-sample the data. The aliasing artifact caused by under-sampling may be separated via the sensitivity map.

The sensitivity map may be obtained based on the data collected by the three-dimensional low resolution complete sampling.

To be specific, the data of the target objected collected by the three-dimensional low resolution complete sampling may be obtained, wherein the data of the target objected may be collected based on a sixth three-dimensional magnetic resonance imaging sequence. Further, the sensitivity map may be calculated and obtained based on the data collected by the three-dimensional low resolution complete sampling. The sensitivity map may be obtained by applying a technique of eigenvalue iterative self-steady in parallel imaging reconstruction to calculate the data collected by the three-dimensional low resolution complete sampling.

The data collected by the three-dimensional low resolution complete sampling and the three-dimensional under-sampling data may have a same view.

Of course, the sixth three-dimensional magnetic resonance imaging sequence may be the TSE sequence, the three-dimensional bSSFP sequence, or the like.

In an operation of S104, image reconstruction may be performed to the three-dimensional under-sampling data by taking the three-dimensional point spread function and the sensitivity map, and the reconstructed magnetic resonance image may be obtained.

Calibrating the trace of the space K may be performed to the three-dimensional under-sampling data through the three-dimensional point spread function. Each layer of the image may be separated from the aliasing image through the sensitivity map to obtain the reconstructed magnetic resonance image. The reconstructed magnetic resonance image may be calculated and obtained based on a following formula:

$$recon(x, y, z) = C(x, y, z) \cdot F_x^{-1} \frac{F_x wave(x, y, z)}{M \cdot PSF_{yz}(k_x, y, z)}$$

In the above formula, the wave(x, y, z) may be the three-dimensional under-sampling data. The M may be an aliasing matrix based on 2D CAIPIRINHA. The $F_x$ and $F_x^{-1}$ may be a one-dimensional Fourier transformation and inverse-Fourier transformation. The recon(x, y, z) may be the reconstructed magnetic resonance image. The $PSF_{yz}(k_x, y, z)$ may be the three-dimensional point spread function, and the C(x, y, z) may be the sensitivity map.

A sequence of the operations of the above-mentioned method may be an available sequence of the operations in the present embodiment. It may be understood that, a sequence of obtaining the three-dimensional point spread function, the sensitivity map, and the three-dimensional under-sampling data may be interchangeable.

In the present embodiment, the wave-CAIPI may be applied in the first three-dimensional magnetic resonance imaging sequence, and the first sinusoidal gradient field may be applied within the duration of the reading platform of the reading gradient field. The 0-order moment of the first sinusoidal gradient field and the 0-order moment of the second sinusoidal gradient field may be 0. In this way, the scanning speed of the magnetic resonance may be increased, and at the same time, the first sinusoidal gradient field and the second sinusoidal gradient field may not interfere the magnetic resonance signal generated by the target object based on the first magnetic resonance imaging sequence within a repeated period of time, such that the additional artifact may not be introduced into the reconstructed magnetic resonance image.

In order to show practicability and a technical effect of the technical solution provided in the present disclosure, a test is performed to a phantom and a human brain using a 3T magnetic resonance system (MAGNETOM, Siemens AG, Erlangen, Germany).

Figure 14A:
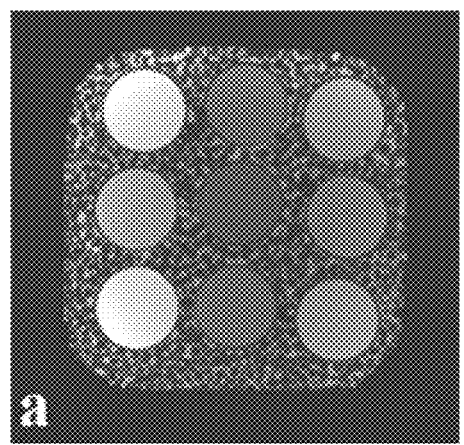
FIG. 14a is a result of a 2×2 times of acceleration test on a phantom using a complete sampled three-dimensional bSSFP sequence.
Figure 14B:
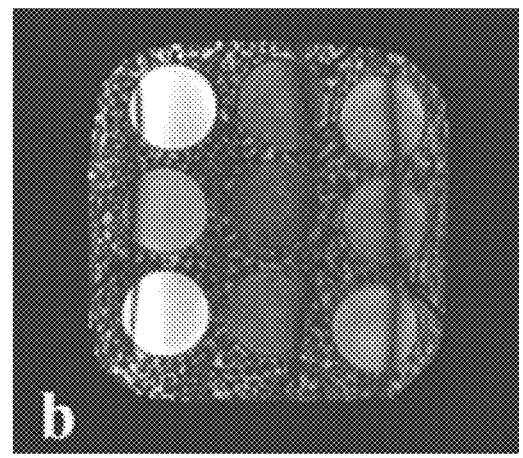
FIG. 14b is a result of a 2×2 times of acceleration test on a phantom using a bSSFP sequence by applying the wave-CAIPI technique.
Figure 14C:
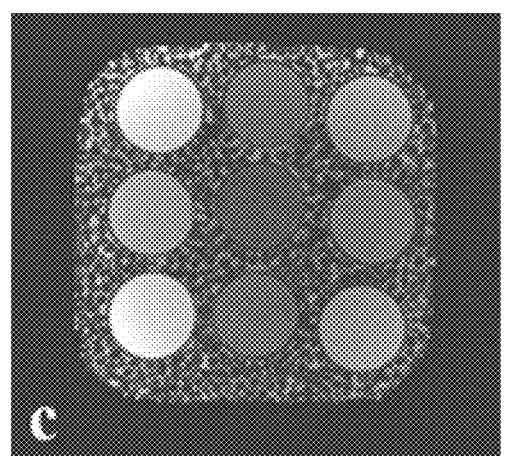
FIG. 14c is a reconstructed image obtained by applying magnetic resonance according to an embodiment of the present disclosure.

As shown in FIGS. 14a to 14c, results of a 2-2 times of acceleration test on a phantom are shown. FIG. 14a shows a reconstructed image based on a complete sampled three-dimensional bSSFP sequence. FIG. 14b shows a reconstructed image based on applying the wave-CAIPI technique to the bSSFP sequence. FIG. 14c shows a reconstructed image obtained by applying the magnetic resonance provided in the embodiments of the present disclosure. Common scanning parameters may be: Echo time=3.23 ms, Repeated time=6.45 ms, a Flip angle=30°, a bandwidth=300 Hz/pixel, a voxel size=1×1×1 mm$^3$, and a scanning matrix size=160×160×72. When applying the wave-CAIPI to the three-dimensional bSSFP sequence, the number of periods of the sinusoidal gradient field along the layer selection direction may be 11, the number of periods of the sinusoidal gradient field along the phase direction may be 11.5, an amplitude value may be 6 mT/m, and an acceleration may be 2×2 times. According to the magnetic resonance imaging method of the present disclosure, the number of sinusoidal periods of the first sinusoidal gradient field may be 10, the number of sinusoidal periods of the second sinusoidal gradient field may be 11, the amplitude value may be 6 mT/m, and the acceleration may be 2×2 times. It may be seen that, applying the wave-CAIPI to the bSSFP sequence may introduce a strip-shaped artifact significantly. However, according to the present disclosure, the 0-order moment of the first sinusoidal gradient field and the 0-order moment of the second sinusoidal gradient field provided may be 0, and applying the first sinusoidal gradient field and the second sinusoidal gradient field to accelerate the bSSFP sequence does not cause the artifact.

Figure 15A:
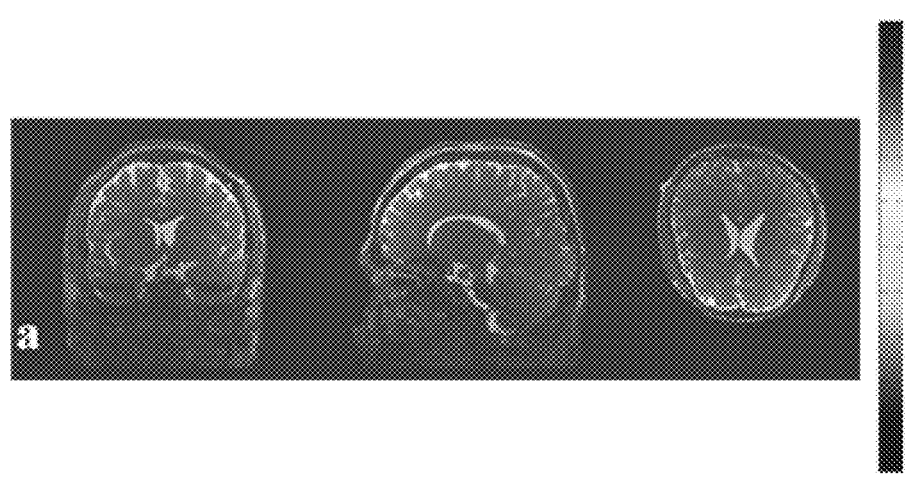
FIG. 15a shows a reconstructed coronal human brain image, a reconstructed sagittal human brain image, and a reconstructed transaxial human brain image, obtained by applying the magnetic resonance imaging method to a balanced Steady-State Free Precession (bSSFP) sequence.
Figure 15B:
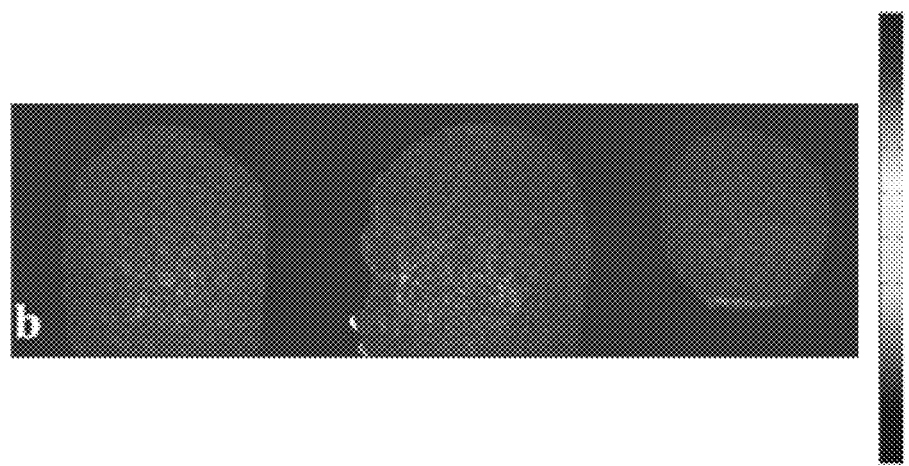
Figure 15C:
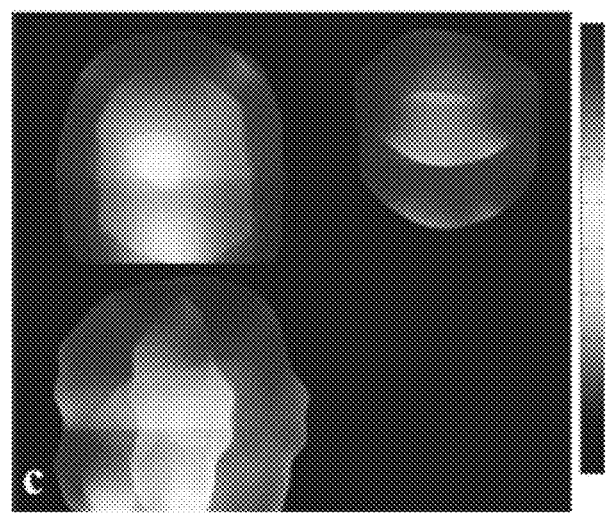

As shown in FIGS. 15a to 15c, images of a human brain obtained by applying the magnetic resonance imaging method to a three-dimensional bSSFP sequence are shown. Scanning parameters include: Echno time=3.36 ms, Repeated time=6.72 ms, a flip angle=300, a bandwidth=299 Hz/pixel, a voxel size=0.8×0.8×0.8 mm$^3$, a scanning matrix size=288×288×240, the number of periods of the first sinusoidal gradient field=4, the number of periods of the second sinusoidal gradient field=5, an amplitude=12.5 mT/m, and an acceleration=4×3 times. FIG. 15a shows a reconstructed coronal human brain image, a reconstructed sagittal human brain image, and a reconstructed transaxial human brain image. FIG. 15b shows corresponding residual images. FIG. 15c shows corresponding images of 1/g-factor. According to the results of the human brain scanning, the method provided in the present disclosure may allow the high-power acceleration of scanning with high resolution to be achieved, and at the same time, allow the artifact caused by the wave-CAIPI to be eliminated.

Figure 16:
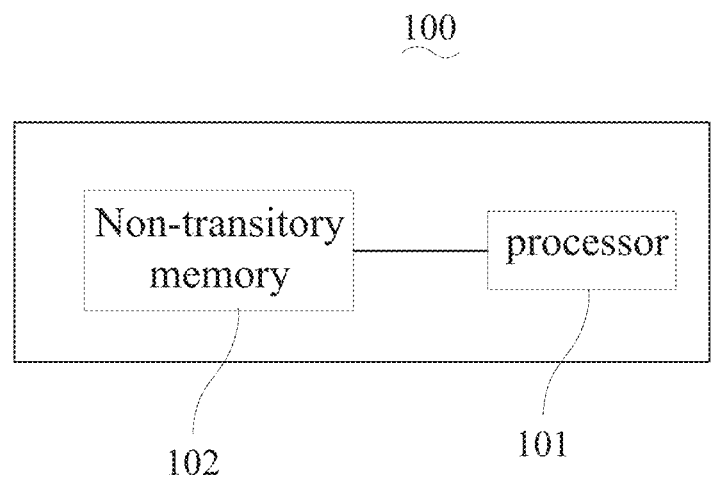
FIG. 16 is a structural schematic view of a magnetic resonance imaging apparatus according to an embodiment of the present disclosure.

The above-mentioned magnetic resonance method may be achieved by a magnetic resonance imaging apparatus. Therefore, the present disclosure may further provide a magnetic resonance imaging apparatus as shown in FIG. 16. FIG. 16 is a structural schematic view of the magnetic resonance imaging apparatus according to an embodiment of the present disclosure. The magnetic resonance imaging apparatus 100 in the present embodiment may include a processor 101 and a non-transitory memory 102 connected to the processor 101. The non-transitory memory 102 may be configured to store the three-dimensional under-sampling data, the two-dimensional mapping data, and the sensitivity map of the target object collected based on the first three-dimensional magnetic resonance imaging sequence. The first three-dimensional magnetic resonance imaging sequence may have a first sinusoidal gradient field on the phase direction and a second sinusoidal gradient field on the layer selection direction. The duration of the first sinusoidal gradient field and the duration of the second sinusoidal gradient field may be within the duration of the reading platform of the reading gradient field applied on the reading direction. The 0-order moment of the first sinusoidal gradient field and the 0-order moment of the second sinusoidal gradient field may be 0, and a phase difference between the first sinusoidal gradient field and the second sinusoidal gradient field may be a/2. The two-dimensional mapping data and the three-dimensional under-sampling data may have a same field of view. The processor 101 may be configured to: obtain the three-dimensional under-sampling data of the target object; calculate and obtain a three-dimensional point spread function based on the three-dimensional under-sampling data or the two-dimensional mapping data; obtain a sensitivity map of the target object; perform image reconstruction to the three-dimensional under-sampling data based on the three-dimensional point spread function and the sensitivity map to obtain the reconstructed magnetic resonance image.

The processor 101 may be an integrated circuit chip, having a capability to process a signal. The processor 101 may also be a general processor, a digital signaling processor, an application specific integrated circuit (ASIC), a field programmable gate array (FPGA), or other programmable logic devices, a discrete gate or transistor logic device, or a discrete hardware assembly. The general processor may be a micro-processor or any conventional processor.

Figure 17:
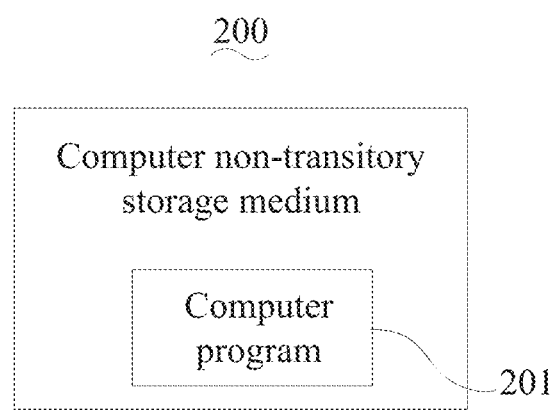
FIG. 17 is a structural schematic view of a computer non-transitory storage medium according to an embodiment of the present disclosure.

The method described in the above-mentioned embodiments may be in a form of computer software. Therefore, the present disclosure may further provide a computer non-transitory storage medium. As shown in FIG. 17, FIG. 17 is a structural schematic view of a computer non-transitory storage medium according to an embodiment of the present disclosure.

The non-transitory storage medium 200 of the present embodiment may store a computer program 201, and the computer program 201 may be executed to achieve the method described in the above-mentioned embodiments.

The computer non-transitory storage medium 200 may be a medium able to store a program instruction, such as a universal serial bus (USB) disc, a portable hard disc drive, a read-only memory (ROM), a random access memory (RAM), a magnetic disc, an optical disc, or the like, or may be a server storing the program instruction. The server may send the stored program instruction to another device, and the another device may run the program instruction. Alternatively, the server may run the program instruction.

According to various embodiments of the present disclosure, it may be understood that, the method and the apparatus may be achieved by other means. For example, the implementations of the above-mentioned apparatus may be exemplary only. For example, modules and units may be defined based on logic functions only. Practically, the modules and the units may be defined by other means. For example, a plurality of units or assemblies may be combined or integrated into another system, some features may be omitted or not performed. Further, coupling, indirect coupling, or communicative connection between the shown and discussed features may be achieved by some interfaces. The coupling or communicative connection between apparatuses and units may be electrical, mechanical, or in other forms.

The units that are illustrated separately may be or may not be physically separated. The element shown as a unit may be or may not be a physical unit. That is, the element may be arranged at a position or distributed into various network units. According to actual needs, a part of, or all of, the various network units may be selected to achieve the objective of the present technical solution.

Further, in various embodiments of the present disclosure, various functional units may be integrated into one processing unit. Alternatively, the various functional units may be configured individually. Alternatively, two or more units may be integrated into one unit. The integrated unit may be achieved in a form of hardware or in a form of software.

When the integrated unit is achieved in the form of software and sold or used as an independent product, the product may be stored in a computer-readable non-transitory storage medium. Accordingly, the essence of the technical solution of the present disclosure, a portion of the technical solution contributing to the related art, or the entire technical solution may be achieved in the form of software. The computer software may be stored in the non-transitory storage medium and include a plurality of instructions to enable a computing device (a personal computer, a server, a network device, and the like) or a processor to execute all of or a part of operations of the method described in the various embodiments of the present disclosure. The above-mentioned non-transitory storage medium may include a medium able to store a program code, such as a universal serial bus (USB) disc, a portable hard disc drive, a read-only memory (ROM), a random access memory (RAM), a magnetic disc, an optical disc, or the like.

The above description may be implementations of the present disclosure, but does not limit the scope of the present disclosure. Any equivalent structural or process transformation based on the specification and the drawings, applied directly and indirectly in other related art, should be within the scope of the present disclosure.

What is claimed is:

1. A magnetic resonance imaging method, comprising:
   obtaining three-dimensional under-sampling data of a target object,
   wherein the three-dimensional under-sampling data is collected based on a first three-dimensional magnetic resonance imaging sequence;
   the first three-dimensional magnetic resonance imaging sequence has a first sinusoidal gradient field on a phase direction and a second sinusoidal gradient field on a layer selection direction;
   a duration of the first sinusoidal gradient field and a duration of the second sinusoidal gradient field are within a duration of a reading platform of a reading gradient field, wherein the reading gradient field is applied on a reading direction;
   a 0-order moment of the first sinusoidal gradient field and a 0-order moment of the second sinusoidal gradient field are 0; and
   a phase difference between the first sinusoidal gradient field the second sinusoidal gradient field is $\pi/2$;
   calculating and obtaining a three-dimensional point spread function based on the three-dimensional under-sampling data or two-dimensional mapping data of the target object, wherein the two-dimensional mapping data and the three-dimensional under-sampling data have a same field of view;
   calculating and obtaining a sensitivity map of the target object based on data of the target object collected by three-dimensional complete sampling; and
   performing image reconstruction to the three-dimensional under-sampling data based on the three-dimensional point spread function and the sensitivity map to obtain a reconstructed magnetic resonance image.

2. The method according to claim 1, wherein a sinusoidal frequency of the first sinusoidal gradient field is equal to a sinusoidal frequency of the second sinusoidal gradient field.

3. The method according to claim 1, wherein
   the two-dimensional mapping data comprises a first two-dimensional mapping data of the target object collected based on a second three-dimensional magnetic resonance imaging sequence, a second two-dimensional mapping data of the target object collected based on a third three-dimensional magnetic resonance imaging sequence, a third two-dimensional mapping data of the target object collected based on a fourth three-dimensional magnetic resonance imaging sequence, and a fourth two-dimensional mapping data of the target object collected based on a fifth three-dimensional magnetic resonance imaging sequence;
   the second three-dimensional magnetic resonance imaging sequence comprises the first sinusoidal gradient field and a first gradient field on the phase direction; the third three-dimensional magnetic resonance imaging sequence comprises the first gradient field on the phase direction; the fourth three-dimensional magnetic resonance imaging sequence comprises the second sinusoidal gradient field and the first gradient field on the layer selection direction; the fifth three-dimensional magnetic resonance imaging sequence comprises the first gradient field on the layer selection direction; and
   the calculating and obtaining the three-dimensional point spread function based on the two-dimensional mapping data of the target object comprises:
   dividing the first two-dimensional mapping data by the second two-dimensional mapping data to obtain a two-dimensional point spread function of the phase direction;
   dividing the third two-dimensional mapping data by the fourth two-dimensional mapping data to obtain a two-dimensional point spread function of the layer selection direction; and
   obtaining the three-dimensional point spread function based on the two-dimensional point spread function of the phase direction and the two-dimensional point spread function of the layer selection direction.

4. The method according to claim 3, wherein the obtaining the sensitivity map of the target object comprises:
   obtaining data of the target object collected by three-dimensional complete sampling, wherein the data is collected based on a sixth three-dimensional magnetic resonance imaging sequence, and the data collected by three-dimensional complete sampling and the three-dimensional under-sampling data have a same field of view; and
   calculating and obtaining the sensitivity map based on the data collected by three-dimensional complete sampling.

5. The method according to claim 4, wherein the calculating and obtaining the sensitivity map based on the data collected by three-dimensional complete sampling comprises:

calculating the data collected by three-dimensional complete sampling by performing eigenvalue iterative self-steady in parallel imaging reconstruction to obtain the sensitivity map.

6. The method according to claim 4, wherein the sixth three-dimensional magnetic resonance imaging sequence is a three-dimensional gradient echo sequence, a turbo spin echo sequence, or a three-dimensional balanced steady-state free precession sequence.

7. The method according to claim 1, wherein the three-dimensional under-sampling data is obtained by performing under-sampling to collect a magnetic resonance signal, the magnetic resonance signal is generated by the target object based on the first three-dimensional magnetic resonance imaging sequence, and performing under-sampling is performing controlled aliasing in parallel imaging results in higher acceleration, performing sensitivity encoding in parallel imaging, or performing generalized autocalibrating partially parallel acquisitions.

8. The method according to claim 4, wherein the first three-dimensional magnetic resonance imaging sequence is obtained by applying the first sinusoidal gradient field on the phase direction and applying the second sinusoidal gradient field on the layer selection direction based on a seventh three-dimensional magnetic resonance imaging sequence; the seventh three-dimensional magnetic resonance imaging sequence is a three-dimensional balanced steady-state free precession sequence, a three-dimensional gradient echo sequence, a turbo spin echo sequence, a magnetization-prepared rapid gradient echo sequence, or a visualization of short transverse relaxation time component sequence.

9. A magnetic resonance imaging apparatus, comprising a processor and a non-transitory memory, wherein the processor is coupled to the non-transitory memory, the processor is configured to execute an instruction and work with the non-transitory memory cooperatively to perform operations of:
obtaining three-dimensional under-sampling data of a target object,
wherein the three-dimensional under-sampling data is collected based on a first three-dimensional magnetic resonance imaging sequence;
the first three-dimensional magnetic resonance imaging sequence has a first sinusoidal gradient field on a phase direction and a second sinusoidal gradient field on a layer selection direction;
a duration of the first sinusoidal gradient field and a duration of the second sinusoidal gradient field are within a duration of a reading platform of a reading gradient field, wherein the reading gradient field is applied on a reading direction;
a 0-order moment of the first sinusoidal gradient field and a 0-order moment of the second sinusoidal gradient field are 0; and
a phase difference between the first sinusoidal gradient field the second sinusoidal gradient field is $\pi/2$;
calculating and obtaining a three-dimensional point spread function based on the three-dimensional under-sampling data or two-dimensional mapping data of the target object, wherein the two-dimensional mapping data and the three-dimensional under-sampling data have a same field of view;
calculating and obtaining a sensitivity map of the target object based on data of the target object collected by three-dimensional complete sampling; and
performing image reconstruction to the three-dimensional under-sampling data based on the three-dimensional point spread function and the sensitivity map to obtain a reconstructed magnetic resonance image.

10. The magnetic resonance imaging apparatus according to claim 9, wherein a sinusoidal frequency of the first sinusoidal gradient field is equal to a sinusoidal frequency of the second sinusoidal gradient field.

11. The magnetic resonance imaging apparatus according to claim 9, wherein
the two-dimensional mapping data comprises a first two-dimensional mapping data of the target object collected based on a second three-dimensional magnetic resonance imaging sequence, a second two-dimensional mapping data of the target object collected based on a third three-dimensional magnetic resonance imaging sequence, a third two-dimensional mapping data of the target object collected based on a fourth three-dimensional magnetic resonance imaging sequence, and a fourth two-dimensional mapping data of the target object collected based on a fifth three-dimensional magnetic resonance imaging sequence;
the second three-dimensional magnetic resonance imaging sequence comprises the first sinusoidal gradient field and a first gradient field on the phase direction; the third three-dimensional magnetic resonance imaging sequence comprises the first gradient field on the phase direction; the fourth three-dimensional magnetic resonance imaging sequence comprises the second sinusoidal gradient field and the first gradient field on the layer selection direction; the fifth three-dimensional magnetic resonance imaging sequence comprises the first gradient field on the layer selection direction; and
when calculating and obtaining the three-dimensional point spread function based on the two-dimensional mapping data of the target object, the processor is configured to execute the instruction and work with the non-transitory memory cooperatively to further perform operations of:
dividing the first two-dimensional mapping data by the second two-dimensional mapping data to obtain a two-dimensional point spread function of the phase direction;
dividing the third two-dimensional mapping data by the fourth two-dimensional mapping data to obtain a two-dimensional point spread function of the layer selection direction; and
obtaining the three-dimensional point spread function based on the two-dimensional point spread function of the phase direction and the two-dimensional point spread function of the layer selection direction.

12. The magnetic resonance imaging apparatus according to claim 11, wherein when obtaining the sensitivity map of the target object, the processor is configured to execute the instruction and work with the non-transitory memory cooperatively to further perform operations of:
obtaining data of the target object collected by three-dimensional complete sampling, wherein the data is collected based on a sixth three-dimensional magnetic resonance imaging sequence, and the data collected by three-dimensional complete sampling and the three-dimensional under-sampling data have a same field of view; and
calculating and obtaining the sensitivity map based on the data collected by three-dimensional complete sampling.

13. The magnetic resonance imaging apparatus according to claim 12, wherein when calculating and obtaining the sensitivity map based on the data collected by three-dimensional complete sampling, the processor is configured to execute the instruction and work with the non-transitory memory cooperatively to further perform operations of:

calculating the data collected by three-dimensional complete sampling by performing eigenvalue iterative self-steady in parallel imaging reconstruction to obtain the sensitivity map.

14. The magnetic resonance imaging apparatus according to claim 12, wherein the sixth three-dimensional magnetic resonance imaging sequence is a three-dimensional gradient echo sequence, a turbo spin echo sequence, or a three-dimensional balanced steady-state free precession sequence.

15. The magnetic resonance imaging apparatus according to claim 9, wherein the three-dimensional under-sampling data is obtained by performing under-sampling to collect a magnetic resonance signal, the magnetic resonance signal is generated by the target object based on the first three-dimensional magnetic resonance imaging sequence, and performing under-sampling is performing controlled aliasing in parallel imaging results in higher acceleration, performing sensitivity encoding in parallel imaging, or performing generalized autocalibrating partially parallel acquisitions.

16. The magnetic resonance imaging apparatus according to claim 12, wherein the first three-dimensional magnetic resonance imaging sequence is obtained by applying the first sinusoidal gradient field on the phase direction and applying the second sinusoidal gradient field on the layer selection direction based on a seventh three-dimensional magnetic resonance imaging sequence; the seventh three-dimensional magnetic resonance imaging sequence is a three-dimensional balanced steady-state free precession sequence, a three-dimensional gradient echo sequence, a turbo spin echo sequence, a magnetization-prepared rapid gradient echo sequence, or a visualization of short transverse relaxation time component sequence.

17. A computer non-transitory storage medium, storing a computer program, wherein the computer program is configured to be executed by the processor to perform operations of:

obtaining three-dimensional under-sampling data of a target object,
wherein the three-dimensional under-sampling data is collected based on a first three-dimensional magnetic resonance imaging sequence;
the first three-dimensional magnetic resonance imaging sequence has a first sinusoidal gradient field on a phase direction and a second sinusoidal gradient field on a layer selection direction;
a duration of the first sinusoidal gradient field and a duration of the second sinusoidal gradient field are within a duration of a reading platform of a reading gradient field, wherein the reading gradient field is applied on a reading direction;
a 0-order moment of the first sinusoidal gradient field and a 0-order moment of the second sinusoidal gradient field are 0; and
a phase difference between the first sinusoidal gradient field the second sinusoidal gradient field is $\pi/2$;
calculating and obtaining a three-dimensional point spread function based on the three-dimensional under-sampling data or two-dimensional mapping data of the target object, wherein the two-dimensional mapping data and the three-dimensional under-sampling data have a same field of view;

calculating and obtaining a sensitivity map of the target object based on data of the target object collected by three-dimensional complete sampling; and
performing image reconstruction to the three-dimensional under-sampling data based on the three-dimensional point spread function and the sensitivity map to obtain a reconstructed magnetic resonance image.

18. The computer non-transitory storage medium according to claim 17, wherein a sinusoidal frequency of the first sinusoidal gradient field is equal to a sinusoidal frequency of the second sinusoidal gradient field.

19. The computer non-transitory storage medium according to claim 17, the two-dimensional mapping data comprises a first two-dimensional mapping data of the target object collected based on a second three-dimensional magnetic resonance imaging sequence, a second two-dimensional mapping data of the target object collected based on a third three-dimensional magnetic resonance imaging sequence, a third two-dimensional mapping data of the target object collected based on a fourth three-dimensional magnetic resonance imaging sequence, and a fourth two-dimensional mapping data of the target object collected based on a fifth three-dimensional magnetic resonance imaging sequence;

the second three-dimensional magnetic resonance imaging sequence comprises the first sinusoidal gradient field and a first gradient field on the phase direction; the third three-dimensional magnetic resonance imaging sequence comprises the first gradient field on the phase direction; the fourth three-dimensional magnetic resonance imaging sequence comprises the second sinusoidal gradient field and the first gradient field on the layer selection direction; the fifth three-dimensional magnetic resonance imaging sequence comprises the first gradient field on the layer selection direction; and
when calculating and obtaining the three-dimensional point spread function based on the two-dimensional mapping data of the target object, the computer program is configured to be executed by the processor to perform operations of:
dividing the first two-dimensional mapping data by the second two-dimensional mapping data to obtain a two-dimensional point spread function of the phase direction;
dividing the third two-dimensional mapping data by the fourth two-dimensional mapping data to obtain a two-dimensional point spread function of the layer selection direction; and
obtaining the three-dimensional point spread function based on the two-dimensional point spread function of the phase direction and the two-dimensional point spread function of the layer selection direction.

20. The computer non-transitory storage medium according to claim 19, wherein when obtaining the sensitivity map of the target object, the computer program is configured to be executed by the processor to perform operations of:
obtaining data of the target object collected by three-dimensional complete sampling, wherein the data is collected based on a sixth three-dimensional magnetic resonance imaging sequence, and the data collected by three-dimensional complete sampling and the three-dimensional under-sampling data have a same field of view; and
calculating and obtaining the sensitivity map based on the data collected by three-dimensional complete sampling.

* * * * *